United States Patent [19]

Baier et al.

[11] 3,988,932

[45] Nov. 2, 1976

[54] OIL SLICK SAMPLING APPARATUS AND METHOD

[75] Inventors: Robert E. Baier, Buffalo; Alfred Wright, North Tonawanda, both of N.Y.

[73] Assignee: Calspan Corporation, Buffalo, N.Y.

[22] Filed: May 16, 1975

[21] Appl. No.: 578,281

[52] U.S. Cl. .................... 73/421 R; 210/DIG. 27
[51] Int. Cl.² ........................................ G01N 1/00
[58] Field of Search ............... 61/1 F; 210/40, 59, 210/83, 242, DIG. 21; 252/316; 106/252, 253; 73/290, 294, 305, 421 R

[56] References Cited
UNITED STATES PATENTS

| | | | |
|---|---|---|---|
| 3,369,664 | 2/1968 | Dahan | 210/DIG. 21 |
| 3,645,099 | 2/1972 | Saavedra | 210/DIG. 21 |
| 3,667,609 | 6/1972 | Daniel | 210/DIG. 21 |
| 3,679,058 | 7/1972 | Smith | 210/DIG. 21 |
| 3,703,464 | 11/1972 | Ferm | 210/DIG. 21 |
| 3,748,264 | 7/1973 | McCombie | 210/DIG. 21 |
| 3,762,169 | 10/1973 | Graham | 210/242 |
| 3,810,835 | 5/1974 | Ferm | 210/59 |
| 3,839,870 | 10/1974 | Ryan | 61/1 F |
| 3,850,807 | 11/1974 | Jones | 210/DIG. 21 |
| 3,887,907 | 6/1975 | Brill | 210/DIG. 21 |

*Primary Examiner*—Theodore A. Granger
*Attorney, Agent, or Firm*—Allen J. Jaffe

[57] ABSTRACT

An oil slick sampling apparatus and method wherein a substantially annular hoop-like frame adapted to float on water and surround the slick, has an inner annular surface coacted with a surface active material which functions by spreading to compress the area of the oil slick. According to one embodiment the frame is hollow and has one or more openings to collect the oil slick as it is compressed by the inwardly spreading area of the surface active coating; according to a second embodiment the frame is impervious and the slick is compressed by the surface active material inwardly toward a central area thereof whereat suitable collecting means is located to collect the oil slick for further analysis.

4 Claims, 5 Drawing Figures

OIL SLICK SAMPLING APPARATUS AND METHOD

BACKGROUND OF THE INVENTION

Each year a large number of accidental oil discharges occur in navigable waters, some of which are reported to the appropriate authorities, others are not. These unreported oil discharges generally remain undetected until the appropriate authorities, as a part of anti-pollution patrols, locate the discharge or oil slick. Various laboratory techniques are then used to identify characteristic constituents of oil slick samples in an attempt to locate the potential sources of the unreported oil discharge.

A key element in the identification process is the collection of an adequate sample of the oil slick. Existing methods and apparatus for collection are crude and inefficient and ill suited for deployment from helicopters or other aircraft. Moreover, the problem of sample contamination is ever present in the collection, handling and delivery of the oil slick sample to the laboratory for analysis.

THE PRESENT INVENTION

The foregoing problems are overcome according to the teachings of the present invention which provides a substantially annular or other suitably shaped member having inner and outer surfaces forming closed boundaries and adapted to float on water, at least a portion of the inner surface of the member is wiped or coated with a suitable surface active material (surfactant) which functions upon contact with water to spread from the inner surface of the member to thereby compress the oil slick into a very small thickened area.

According to one embodiment of the present invention the member is hollow and contains one or more openings through which the oil slick is driven and collected by the spreading action of the surfactant.

According to a second embodiment of the present invention the inner surface of the member is impervious and is substantially completely coated with the surfactant whereby the oil slick is driven to a central area within the boundaries of said member and is collected by absorbtion or adsorption to a suitable collection element located in said central area.

The amount of the surfactant employed is so small that its weight is undetectable and spreads in monomolecular thickness on the order of $10^{-7}$ inches whereby no interference with or contamination of the oil slick is possible so as to obscure the analysis thereof with respect to composition, source or age.

BRIEF DESCRIPTION OF THE DRAWINGS

For a fuller understanding of the present invention, reference should now be had to the following detailed description thereof taken in conjunction with the accompanying drawings, wherein.

DESCRIPTION OF THE PREFERRED EMBODIMENTS

Figure 1:
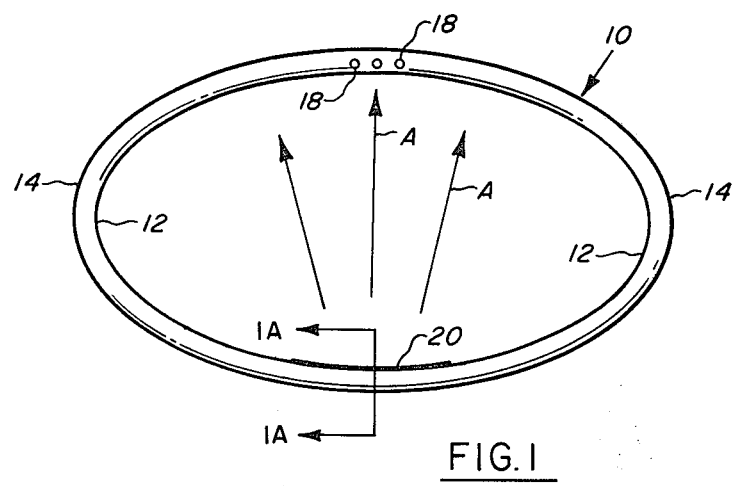
FIG. 1 is a pictorial illustration of one embodiment according to the present invention.

Referring now to the drawings and, more particularly, to FIG. 1, the sampling apparatus comprises a substantially annular frame or tube generally depicted at 10. Frame 10 is adapted to float on water and, accordingly, is fabricated of any suitable material which will permit floatation such as, for example, polyethylene. Since the frame may be hollow, other heavier materials are contemplated as long as the effective specific gravity thereof is less than that of water and greater than that of the oil slick. Frame 10 has substantially continuous exterior inner walls or surfaces 12 and outer exterior surfaces 14 and may be hollow for floatation and/or oil collection, as will become apparent hereinbelow.

Figure 1A:
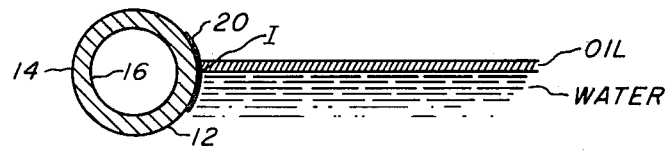
FIG. 1a is a section along line 1A—1A of FIG. 1.

The oil slick floating on the water within the area circumscribed or bounded by inner surfaces 12 is in fluid communication with the hollow interior chamber 16 of the frame 10 by means of one or more ports 18 located on a portion of inner surfaces 12. The portions of surfaces 12 which are remote or diametrically opposed from ports 18 are wiped or coated with a thin layer of a suitable surface active agent or surfactant schematically depicted at 20 in FIG. 1a. It is significant to note that the surfactant 20 is in contact with the oil-water interface I. To this end, the buoyancy of the frame 10 is adjusted such that it floats on the water with inner surfaces 12 being of sufficient depth to contact the oil as well as the water.

In the operation of the FIG. 1 embodiment, the frame 10 may be deployed from a helicopter (not illustrated) into the water in the area of the oil slick. As soon as the surfactant on the inner surfaces 12 contacts the water-oil interface, in a well known manner, the interfacial tension or free energy between the oil and water is modified by the action of the surfactant, which, in turn permits the surfactant to spread in the direction of arrows A in FIG. 1 causing the oil to recede and thicken towards a predetermined area within the boundaries of the frame 10. In this embodiment such area is the vicinity of the ports 18 which permit the oil to be collected interiorly of the hollow frame 10 for further analysis. In other words, the spreading action of the surfactant drives the oil layer into the hollow of frame 10 through ports 18.

As the oil enters the frame, the weight of the frame increases and it floats deeper in the water but since the oil slick has been substantially thickened by the spreading surfactant, the ports still collect mostly oil.

As is well known to those skilled in this art many types of surfactant materials may be employed such as, for example, sorbitan monooleate, oleyl alcohol, oleic acid, "Herder" (Shell Oil Co. Trademark) and others. Although not essential to operation of the present invention, it is preferred that the surfactant have a surface tension depression or surface pressure greater than 30 dynes per centimeter.

Although the frame 10 has been illustrated as circular or annular, other geometric shapes are contemplated so long as the inner surfaces thereof are substantially continuous to define a closed boundary for the water and oil slick. Thus, FIG. 2 illustrates a rectangularly shaped frame 10' comprised of pipe lengths and connecting elbows.

Figure 2:
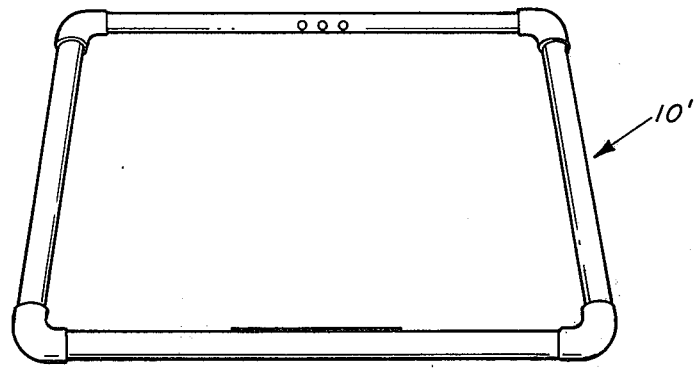
FIG. 2 is a pictorial illustration of a slight variation of the embodiment of FIG,. 1.
Figures 3, 4:
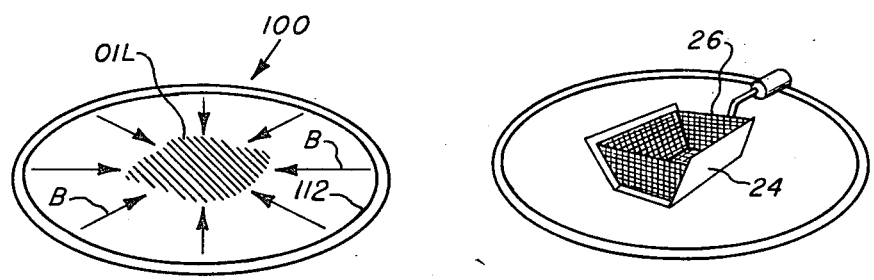
FIG. 3 is a pictorial illustration of a second embodiment according to the present invention.
FIG. 4 is a view similar to FIG. 3 illustrating one technique for removal of the oil slick.

Whereas the embodiments of FIG. 1 and FIG. 2 contemplate the oil slick collection through ports leading to the hollow frame, the embodiment of FIG. 3 and FIG. 4 contemplates separate collection means for the oil slick. To this end, the inner surfaces 112 of frame 100 are impervious and substantially completely wiped or coated with the surfactant. When the surfactant contacts the oil-water interface it spreads, as previously indicated, in the direction of arrows B pushing the oil slick toward a central area of that bounded by frame 100. This pushing action on the slick causes the same to thickness whereby a sample can be easily picked up by absorbtion, adsorption or by mechanical means.

One exemplary technique for collecting the oil slick sample is illustrated in FIG. 4 wherein filter paper 24 or the like located on member 26 is touched to the thickened oil whereupon the same is transferred thereto and collected for further analysis. It is to be understood that other well known collection means can be provided in place of the filter paper, such as any material to which the oil will adhere. Mechanically, a suction tube can be placed in the thickened oil for collection.

Although preferred embodiments of the present invention have been disclosed and described, changes will obviously occur to those skilled in the art; it is therefore intended that the scope thereof is to be limited only by the scope of the appended claims.

We claim:

1. A method of determining the quantity of a lighter liquid floating on an area of determined size of a body of water and collecting the lighter liquid for further analysis, comprising the steps of:
    a. floating a continuous member on the surface of said body of water to surround an area of determined size,
    b. coating with a surfactant at least portions of the peripheral length of said continuous member facing the area surrounded by said member whereby said surfactant is effective to cause the lighter liquid with the area of said continuous member to be directed to a predetermined area,
    c. collecting said lighter liquid at said predetermined area for analysis, and
    d. said continuous member comprising a hollow tube having at least one inlet opening in a portion thereof facing the area surrounded by said member and substantially opposite and spaced from the portions thereof coated with said surfactant whereby said surfactant causes the lighter liquid to be directed toward said inlet opening to be collected thereby.

2. Apparatus for determining the quantity of oil floating on a determined area of the surface of a body of water and collecting the same for analysis, comprising in combination;
    a. a continuous member constructed and arranged to float on the surface of said body of water to surround an area of determined size,
    b. a coating of surfactant applied to at least portions of the peripheral length of said continuous member facing the area surrounded by said member whereby, when said apparatus is floating on the surface of said body of water a lighter liquid floating thereon, said surfactant is effective to cause the lighter liquid within the area of said continuous member to be directed to a predetermined area,
    c. means for collecting said lighter liquid at said predetermined area for analysis,
    d. said member comprising a hollow tube, and
    e. said means for collecting said lighter liquid comprising at least one inlet opening in a portion of said tube facing the area surrounding by said member and substantially opposite and spaced from the portions thereof containing said coating of surfactant whereby said surfactant causes the lighter liquid to be directed toward said inlet opening to be collected thereby.

3. The apparatus according to claim 2, wherein said predetermined area is located centrally of said inner surfaces and said surfactant is located on substantially all of said inner surfaces.

4. Apparatus for determining the quantity of oil floating on a determined area of the surface of a body of water and collecting the same for analysis, comprising in combination;
    a. a continuous member constructed and arranged to float on the surface of said body of water to surround an area of determined size,
    b. a coating of surfactant applied to substantially the entire peripheral length of said continuous member facing the area surrounded by said member, whereby when said apparatus is floating on the surface of said body of water with a lighter liquid floating thereon, said surfactant is effective to cause the lighter liquid within the area of said continuous member to be directed to a central area within said continuous member, and
    c. means for collecting said lighter liquid at said central area comprising a member containing a material to which said lighter liquid adheres when brought into contact therewith.

* * * * *